United States Patent [19]

Webinger

[11] Patent Number: 4,483,095
[45] Date of Patent: Nov. 20, 1984

[54] TELESCOPING CONTAINER

[75] Inventor: George P. Webinger, Robbinsdale, Minn.

[73] Assignee: Champion International Corporation, Stamford, Conn.

[21] Appl. No.: 597,649

[22] Filed: Apr. 6, 1984

Related U.S. Application Data

[63] Continuation-in-part of Ser. No. 529,922, Sep. 6, 1983, abandoned, which is a continuation of Ser. No. 321,018, Nov. 13, 1981, abandoned.

[51] Int. Cl.³ .................... A01M 1/20; A61L 9/04; B65D 5/32
[52] U.S. Cl. ......................... 43/131; 206/525; 229/8; 229/11; 229/23 BT; 229/43; 239/58
[58] Field of Search ............... 206/525; 43/60, 65, 43/107, 118, 131; 229/6 A, 8, 11, 23 BT, 23 R, 43, 45 R; 239/57-60

[56] References Cited

U.S. PATENT DOCUMENTS

| D. 225,892 | 1/1973 | Knies | 229/8 |
|---|---|---|---|
| 2,738,225 | 3/1956 | Meek | 239/60 |
| 3,078,989 | 2/1963 | Curran et al. | 229/8 |
| 3,104,816 | 9/1963 | Jaffe | 239/58 |
| 3,966,112 | 6/1976 | Gordon | 229/23 BT |
| 4,196,843 | 4/1980 | Garmon | 229/45 R |
| 4,219,145 | 8/1980 | Jaeschke et al. | 239/60 |
| 4,277,014 | 7/1981 | Webinger | 229/11 |
| 4,279,373 | 7/1981 | Montealegre | 239/59 |
| 4,280,651 | 7/1981 | Montealegre et al. | 239/59 |
| 4,340,168 | 7/1982 | Webinger | 239/58 |

FOREIGN PATENT DOCUMENTS

2545598 11/1976 Fed. Rep. of Germany ........ 43/131

Primary Examiner—George E. Lowrance
Assistant Examiner—Jimmy G. Foster
Attorney, Agent, or Firm—Evelyn M. Sommer

[57] ABSTRACT

A telescoping container comprising a bottom section having a bottom wall and a plurality of side walls normal to the bottom wall and a cover section having a top wall and a plurality of side walls normal to the top wall; the side walls of the cover section extending on the outside of the corresponding side walls of the bottom section. A flap is externally secured to each of a pair of outer walls of the bottom section and a corresponding flap on corresponding walls extends inwardly of the cover section; this pair of flaps on the inner walls of the cover section passes the corresponding flaps on the outer walls of the base member when the cover section is placed on the bottom section and interlocks when the cover section is withdrawn. The top and bottom walls are caused to be bowed concavely. The bowing of these walls exerts outward forces on the interlocking flaps which, in turn, improves the locking action of the flaps when the cover section is fully extended from the bottom section. The cover member is provided with openings which will make the interior accessible to insects seeking out an insecticide and an attractant placed therein. The size of the openings in the cover section may be adjusted by vertical movement of the cover section to control the degree of exposure of the interior material as, for instance, when the interior material constitutes an air freshener either used alone or in connection with the insecticide.

13 Claims, 9 Drawing Figures

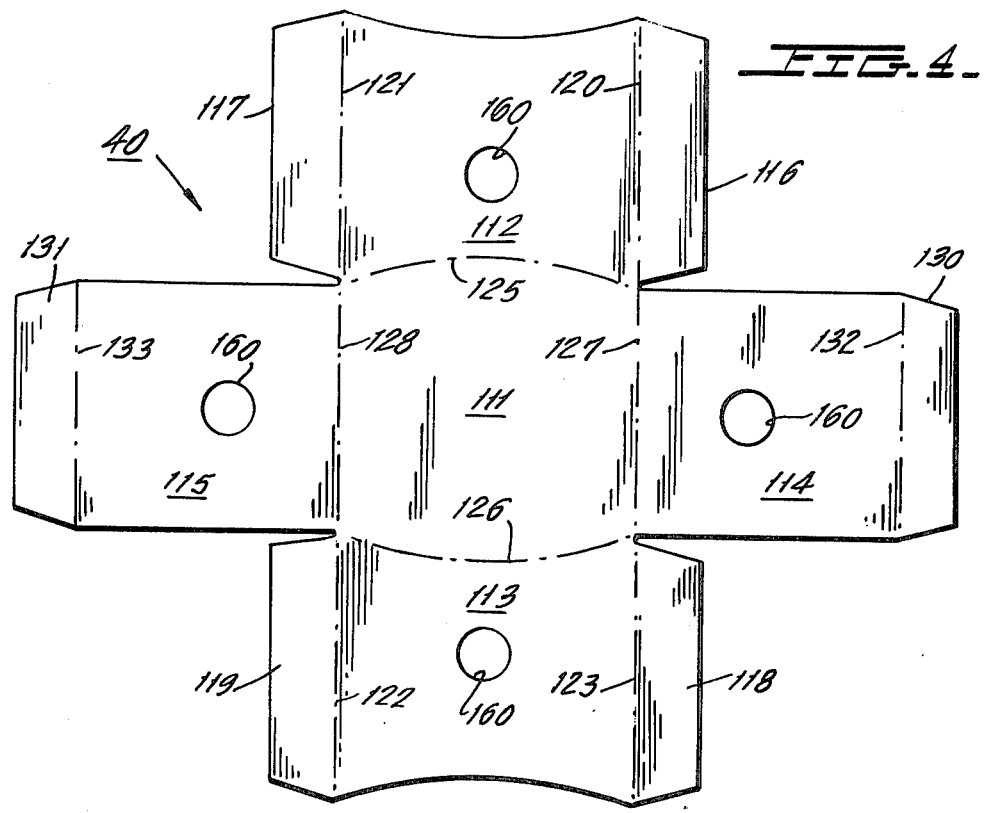
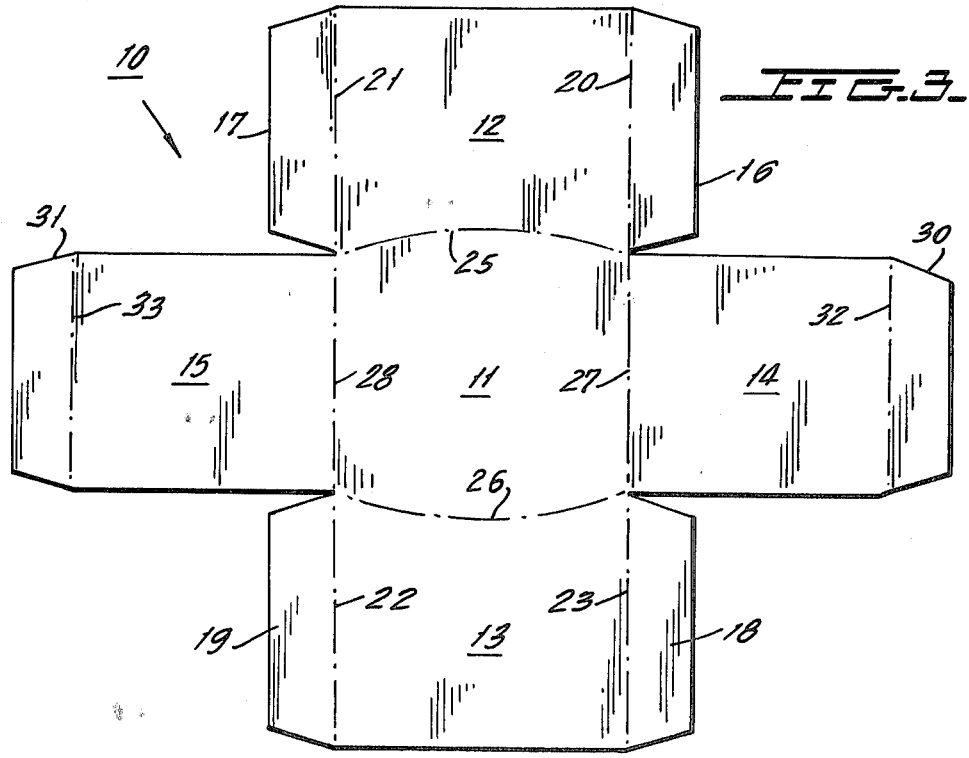

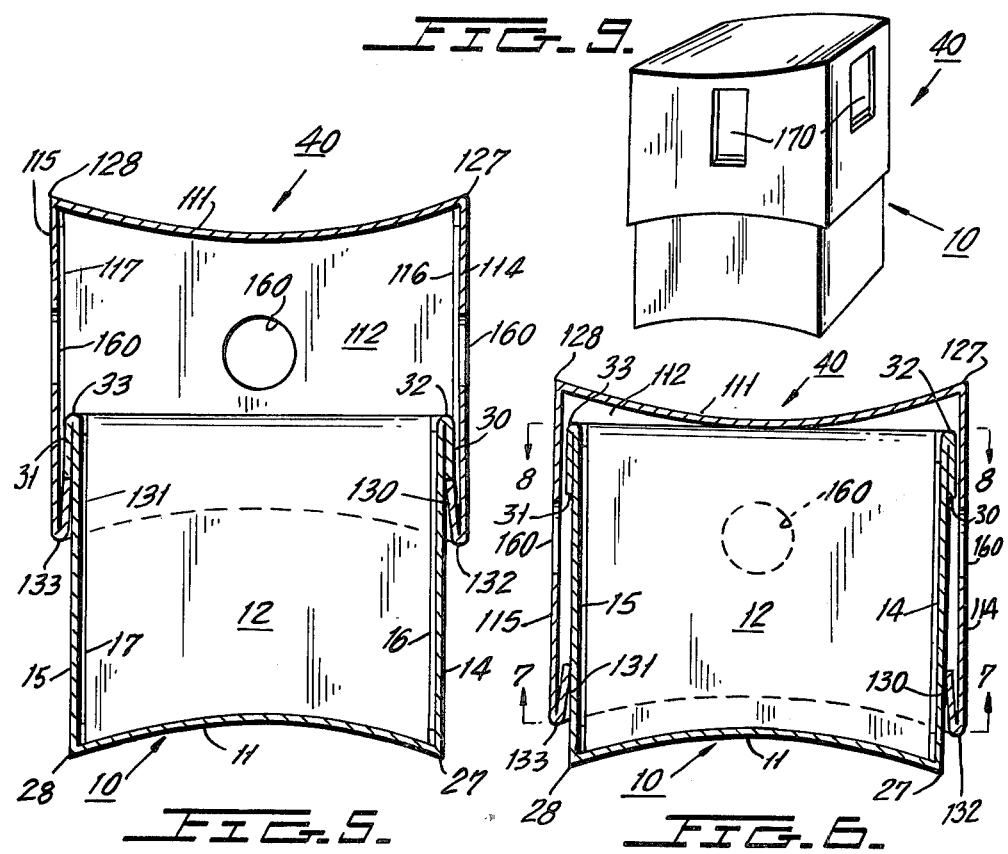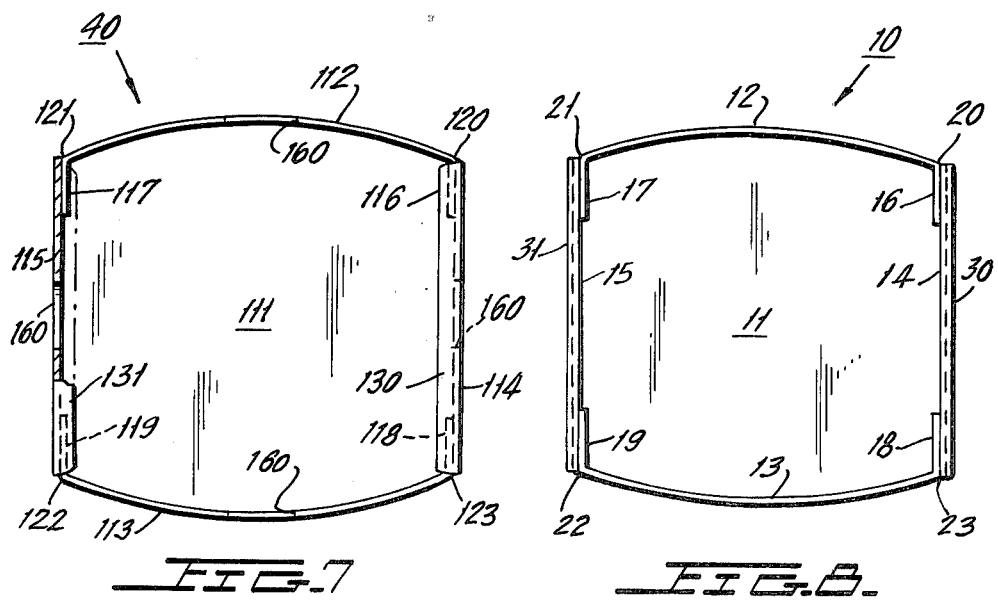

TELESCOPING CONTAINER

This application is a continuation-in-part of U.S. patent application Ser. No. 529,922 filed Sept. 6, 1983, now abandoned, which was a continuation of Ser. No. 321,018 filed Nov. 13, 1981, now abandoned.

The present invention relates to telescoping containers, and more particularly, to a telescoping two-part container having a base section and a cover section which may be slid longitudinally with respect to each other with the cover section being limited in its longitudinal movement so that it will not separate from the base section. The base and cover sections have curved side walls and include concave bottom and top walls, respectively, to facilitate the interengagement of flaps which limit the longitudinal movement. The structure of this telescoping container is such that various materials may be placed therein which may become accessible on the sliding of the cover with respect to the base section.

Essentially, the present invention contemplates an open topped base section having a pair of side walls, end walls and a bottom wall and an open bottom and a cover section having a top wall, side walls, end walls and an open bottom; with the cover section being sufficiently larger in its transverse dimension (parallel to the top) that it may slide readily onto the base section. However, the cover section is so arranged that once the cover section is slid over the base section, movement of the cover section in an outward direction away from the bottom wall of the base section will be limited to the extent that the cover section may not, without manipulation which might destroy the container, be removed from the base section.

Thus when the cover and base section are telescoped together, a fully enclosed container having a single bottom wall and a single top wall and doubled side and end walls are formed. The cover section may be provided with openings so arranged that in a closed condition the openings are blocked off by the side walls and the end walls of the base section. However, the openings may be so spaced on the side walls and end walls of the cover section that when the cover section is moved to its maximum extent to increase the longitudinal distance between the bottom wall of the base section and the top wall of the cover section the openings will clear the side walls and end walls of the base section and thus be accessible.

One of the major fields of utility of a telescoping container of this type is its utilization for various types of environmental control including so-called air fresheners and insecticides. By way of example, an insecticide cylinder or insecticide crystals, pellets, or other material may be placed or secured at the bottom wall of the bottom section and become available to insects when the cover section is moved to a position where the openings therein are no longer blocked by the side walls and end walls of the bottom section. In the case of use for insecticides, the insecticide material may also be combined with an insect attractive material so that the insects will be attracted to the openings and enter through said openings into the interior of the container and be subjected to the effects of the insecticide. In addition to being killed by the insecticide, the insects are then retained at the bottom wall of the base section until all of the insecticide is used up or otherwise has ceased to function. In addition, as mentioned above, an air freshener may be inserted either separately or together with the insecticide so that the air freshener will have some type of deodorant material or material which tends to defeat odors in the immediate vicinity while nevertheless permitting (where used in conjunction with an insecticide) the attractive odor which lures the insect to emanate.

Where the device is used primarily as an insecticide retainer, the openings will be relatively small but, nevertheless, large enough to permit insects to enter readily. But, the area occupied by the openings will be such that insects will not readily be able to find egress until they have come in contact with the insecticide or the insecticide fumes, and will therefore fall to the bottom and be retained by the container. Where used as an air freshener, the openings may be larger or may be arranged longitudinally so that the degree of opening can be more readily controlled.

In addition, the present invention contemplates and it is a primary object of the present invention, in a telescoping container having a top section which telescopes with respect to the bottom section, the provision of openings in the top and the sides of the top section which will become available from the outside to the inside of the container when the cover is slid upwardly away from the bottom wall of the top section.

As a further and corollary object of the present invention, this invention contemplates that a pair of panels on a pair of opposite walls of the bottom section will be secured in position in surface-to-surface relation with the outside of said walls. A pair of panels on corresponding walls of the outer container will be folded inwardly but not secured in surface-to-surface relation, thereby relying on the springiness of the material of which the container is made to bias the pair of panels of the cover inwardly. The cover is a good sliding fit on the bottom wall. Hence, when the cover is placed on the base section, it will slide readily into position. But, since the infolded panels on the inside walls of the cover member will be pushed easily toward the surface of the wall from which they respectively extend, then, on any attempt to remove the cover, these panels, having flexed outwardly somewhat, will engage the edges of the panels which are secured in position at the outside of the base member and thereby interlock the cover and the base so that they cannot be separated. Side panels of the cover member and base member are convexly curved, causing the top and bottom sections thereof, respectively, to be curved concavely. This arrangement facilitates the interengagement of the interlocking panels by increasing the bias of the panels away from their respective walls.

The foregoing and many other objects of the present invention will become apparent from the following description and drawings, in which:

FIG. 3 is a plan view of the blank for forming the base member of FIGS. 1 and 2;

FIG. 4 is a plan view of the blank for forming the cover member of FIGS. 1 and 2;

FIG. 5 is a cross-sectional view taken on line 5—5 of FIG. 2 looking in the direction of the arrows;

FIG. 6 is a cross-section view taken on line 6—6 of FIG. 1 looking in the direction of the arrows;

FIG. 7 is a cross-sectional view taken on line 7—7 of FIG. 6 looking in the direction of the arrows;

FIG. 8 is a cross-sectional view taken on line 8—8 of FIG. 6 looking in the direction of the arrows; and FIG. 9 is a view corresponding to that of FIG. 2 showing, however, a different type of opening which may be used to provide openings of adjustable size in the unit depending on the extent to which the cover member is raised upwardly away from the bottom wall of the base member.

Figure 2:
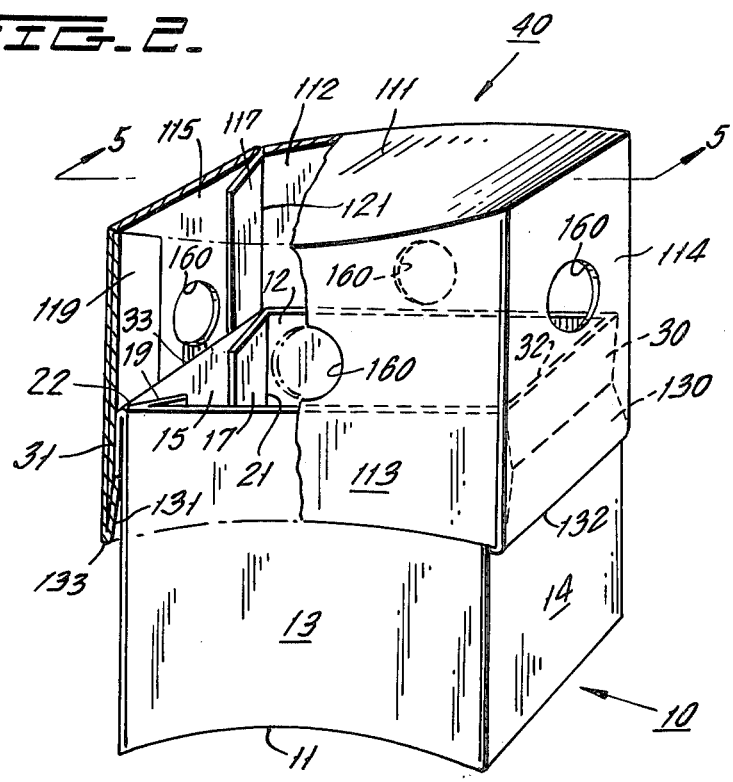
FIG. 2 is a view in perspective corresponding to that of FIG. 1 but showing the cover member slid upwardly with respect to the bottom of the base member exposing the openings in the base member.

Referring now to the Figures, the base member 10 comprises a bottom wall 11, a pair of side walls 12, 13 and a pair of end walls 14, 15. The side walls 12 and 13 are provided with glue panels 16, 17 for the side wall 12 and 18, 19 for the side wall 13 which may be rotated about their respective hinge lines 20, 21, 22, 23 into right angled relation with respect to the side walls 12 and 13 and may be glued to the end walls 14 and 15. Preferably, the gluing will take place by securing the panels 16, 17, 18, 19 to the interior surfaces of the walls 14 and 15 since this enhances the appearance of the container, but they may also be glued to the exterior surfaces of the walls 14, 15.

The side walls 12, 13 are rotatable on the curved hinge line 25 for wall 12 and curved hinge line 26 for wall 13 to a position normal to the bottom wall 11. The use of curved hinge lines 25, 26 will render side walls 12, 13 convex and at the same time force bottom wall 11 into a concave shape. The end walls 14, 15 are rotatable about the hinge line 27 for wall 14 and hinge line 28 for wall 15, also so that they may be normal to the bottom wall 11. When the panels 16, 17, 18, 19 are secured, preferably to the interior of the walls 14, 15, the container is completed, having a bottom wall 11 and an open top.

In addition, interlock panels 30, 31 are provided, interlock panel 30 being connected by the hinge line 32 to the wall 14 and interlock panel 31 being connected by the hinge line 33 to the wall 15. These can be, as seen particularly in FIGS. 2, 5 and 6, adhesively secured to the outside of the walls 14, 15, but do not have to be adhesively secured.

The utilization of the arcuate bend lines 25, 26 ensure that walls 12 and 13 in particular will be curved convexly while the bottom wall 11 will be curved concavely. By ensuring that bottom wall 11 is curved concavely, additional spring bias will be imparted to interlock panels 30, 31 which will result in an improved locking function. The convex curvature of the walls 12 and 13 also permits a cylindrical luring element to be inserted which also has insecticidal properties. However, the member must be sufficiently smaller than the container itself so that insects will have room to fly in.

Where the box is used to contain, for instance, a room freshening material, then the spacing of the interior material provided from the walls must be such as to permit some air to flow from the outside through at least some of the openings past the freshening material and then, through other openings, to outside of the container.

The cover member 40 as seen in the blank of FIG. 4 and also in the other drawings has exactly the same elements as the base member 10 and, hence, has been given the same reference numbers plus 100. There are, however, two major differences.

The first difference is that the flap 130 on wall 114 and the flap 131 on wall 115 are not glued down, but are folded over and turned inwardly toward the walls 114, 115. The fact that they are not secured to the inner surface of the walls 114, 115 permits the inherent resiliency of the material of which the container is made to cause these flaps to bow outwardly slightly, thereby establishing an interlock as seen by a comparison of FIGS. 6 and 5 where FIG. 6 shows the closed container and FIG. 5 shows the container telescoped to the open position. That is, the flaps 130, 131 coact with and interengage the flaps 30, 31 of the base so that the cover member cannot be withdrawn from the base. However, the cover member may readily be slipped onto the base after appropriate material has been placed in the base to facilitate manufacturing. But once slipped on, the interlock is complete and, while, of course, anything can be torn apart in normal usage, the cover cannot be removed from the base. As noted above, the provision of concave top and bottom walls 111 and 11, respectively will cause an increased bias to be imparted to interlock panels 130, 131 and 30, 31 to facilitate the interengagement of the flaps when the cover is slid apart from the base.

While, preferably, the flaps 130, 131 are not glued to the inner walls 114, 115, where a close enough fit is provided between the cover member and the base, then even if these flaps are secured to the inner walls 114, 115 the thickness of the material and inward bias thereon will be such as shown particularly in FIG. 5 to prevent a separation from occurring.

Figure 1:
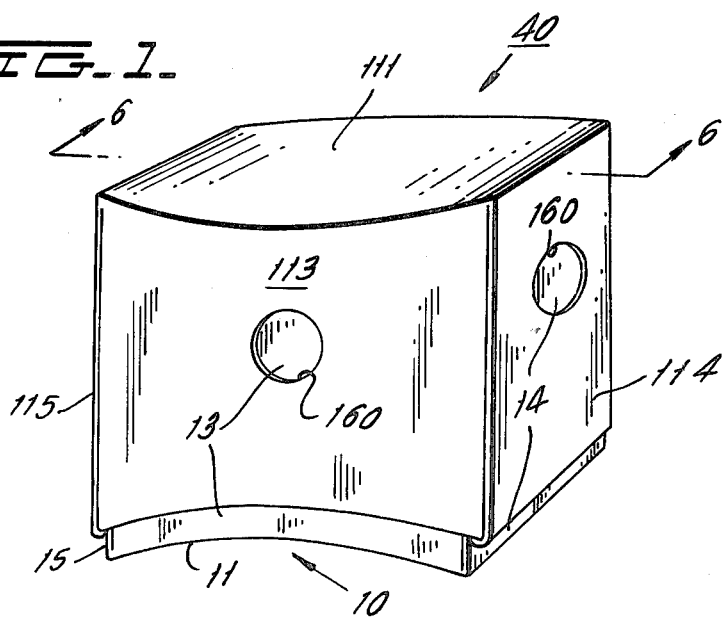
FIG. 1 is a view in perspective of the novel telescoping container of the present invention in its closed position.

It will thus be seen that when the container carrying the material (preferably mounted in the bottom section 10) which acts as an insecticide, insect attractor or air freshener, or for any other purpose, becomes available when the cover member is slid from the position of FIGS. 1 and 6 to the position of FIGS. 2 and 5. The attraction and consequent using up of the material contained within the telescoping container ceases when the cover member 40 is pushed down from the position of FIGS. 2 and 5 to the position of FIGS. 1 and 6.

It will also be seen that the openings 160 provided in the four walls of the cover member become available to the atmosphere when the cover member is raised from the position of FIGS. 1 and 6 to the position of FIGS. 2 and 5 and are closed off when the cover member is pushed back to the position of FIGS. 2 and 6.

It will be obvious now that if only a portion of each of the openings 160 becomes available, then where the device is used, for instance, as an air freshener, less of the material contained within the receptacle will be available for emanation into the atmosphere.

In order to take advantage of the fact that the cover member 40 slides, then, as shown in FIG. 9, instead of using openings 160, which are perforations it is possible to use elongated openings 170. The fact that the openings are elongated permits a substantial adjustment of the size of the opening for various positions of the cover with respect to the base so that the base may be moved vertically a small distance in order to provide a relatively small opening and its full distance in order to provide relatively large openings and the size of the openings between small and large may readily be adjusted.

While the foregoing receptacle has been described as particularly useful in connection with insecticides and particularly in connection with some cylindrical insecticidal body which may substantially fill the container but leave sufficient distance from the openings to permit insects to enter, and while the receptacle has also been described as being able, instead, to contain various types of material, pellets, crystals or other elements which may have insecticidal effect as pointed out above, attractant materials may also be used in conjunction with the insecticidal materials in order to lure insects to the openings. In addition, the receptacle may be used to contain an air freshening type material, either alone or in conjunction with insecticidal material so that the net effect of the utilization of the container will be to provide either a pleasing aroma or to destroy aromas in the immediate vicinity.

It is also obvious that other elements may be included in the container which will have other results and perform other functions, and that the container may be ornamented in some way as, for instance, with openings that simulate a so-called pumpkin head with a light contained therein so that the eyes which would constitute the perforations may be set to different apparent expressions by raising or lowering the cover to a desired degree.

In the foregoing, the present invention has been described solely in connection with preferred illustrated embodiments thereof. Since many modifications and variations of the present invention will now be obvious to those skilled in the art, it is preferred that the scope of the present invention be determined not by the specific disclosures herein contained, but only by the appended claims.

What is claimed is:

1. A telescoping container comprising two sections, each of the sections having a transverse wall, a pair of side walls and a pair of end walls normal to the transverse wall and an open end at the end opposite the transverse wall,
   one of said container sections having a dimension such that it may be slid over and receive the other section;
   the two sections being telescopically arranged with respect to each other with the open end of one section receiving the open end of the other section and the transverse walls being on the outside and parallel to each other so that said sections may be telescoped one within the other from a maximum dimension wherein said transverse walls are farthest from each other to a minimum dimension wherein said transverse walls are closest to each other;
   a pair of flaps at the edges of the end walls of the section which is received within the other section bent back into surface-to-surface relation with the outer surface of said end walls;
   a pair of flaps on the edges of the corresponding end walls of the outer section being bent inwardly to surface-to-surface relation with the inner suface of said end walls; said sections, when telescoping together, being so arranged that said flaps may interengage when the sections are pulled apart to their maximum dimension; the interengagement of said flaps when the telescoping sections are pulled apart preventing the outer section from being withdrawn from the inner section, and
   at least said side walls being connected to each of the transverse walls of each of the container sections by convexly curved fold lines; said curved fold lines causing at least said side walls to curve outwardly to provide a container section which is at least in part cylindrical in shape; said two container sections forming said telescoping container being similarly curved; said curved fold lines further causing said transverse wall in each of said container sections to curve concavely thereby facilitating the interengagement of said flaps.

2. The telescoping container of claim 1, wherein the pair of flaps on the outer wall of the inner section are secured to said outer wall of said inner section.

3. The telescoping container of claim 2, wherein the pair of flaps on the inner surface of the end walls of the outer section are resiliently biased toward the end wall of the inner section; said last mentioned pair of flaps engaging the edges of said first mentioned pair of flaps when the telescoping container is pulled apart to its maximum dimension.

4. The telescoping container of claim 1, wherein at least one opening is provided in a wall of one of said sections; said opening being closed when the container is telescoped to its minimum dimension and being opened when said container is telescoped to its maximum dimension.

5. The telescoping container of claim 1, wherein a plurality of openings is provided in walls of one of said sections; said plurality of openings being closed when said telescoping container is collapsed to its minimum dimension and being open when said container is extended to its maximum dimension.

6. The telescoping container of claim 1, wherein a plurality of openings is provided in all of the walls of one of said sections; said openings being closed when said telescoping container is collapsed to its minimum dimension and being open when said container is extended to its maximum dimension.

7. The telescoping container of claim 1, wherein a plurality of openings is provided in the walls of the outer section, said plurality of openings being closed when said telescoping container is collapsed to its minimum dimension and being open when said container is extended to its maximum dimension.

8. The telescoping container of claim 4, wherein said opening may be fully closed and selectively partially closed and partially opened in accordance with the degree to which said telescoping container is positioned between said minimum and maximum dimensions.

9. The telescoping container of claim 1, wherein a cylindrical element is contained within said telescoping container being secured to a transverse wall of one of said sections.

10. The telescoping container of claim 1, wherein a cylindrical element is contained within said telescoping container being secured to a transverse wall of said inner section.

11. The telescoping container of claim 4, wherein insecticidal material is included in said container and the interior of said container is available for entry of insects when said opening becomes accessible to the interior of the container on movement of the two sections of the container toward its maximum dimension.

12. The telescoping container of claim 4, wherein air freshening material is contained within said telescoping container and becomes available to the atmosphere through said opening when the telescoping container is moved toward its maximum dimension.

13. The telescoping container of claim 4, wherein the size of the opening which becomes available to the atmosphere is determined by the extent to which said telescoping container is moved between said maximum and minimum dimension.

* * * * *